US 6,281,237 B1

(12) United States Patent
Horvath et al.

(10) Patent No.: US 6,281,237 B1
(45) Date of Patent: Aug. 28, 2001

(54) N-PHENYL BENZIMIDAZOLECARBOXAMIDE AND N-PHENYL INDOLECARBOXAMIDE DERIVATIVES

(75) Inventors: Raymond F. Horvath, North Branford; Ping Ge, Branford; Taeyoung Yoon, East Haven; Alan Hutchison, Madison, all of CT (US)

(73) Assignee: Neurogen Corporation, Brandford, CT (US)

( * ) Notice: Subject to any disclaimer, the term of this patent is extended or adjusted under 35 U.S.C. 154(b) by 0 days.

(21) Appl. No.: 09/540,478

(22) Filed: Mar. 31, 2000

Related U.S. Application Data

(60) Provisional application No. 60/127,624, filed on Apr. 1, 1999.

(51) Int. Cl.[7] .................... A61K 31/4184; C07D 235/14
(52) U.S. Cl. .................. 514/394; 514/419; 548/309.7; 548/495
(58) Field of Search ................ 548/309.7; 514/394

(56) References Cited

U.S. PATENT DOCUMENTS

| 3,255,202 | * | 6/1966 | Johnson | 260/309.2 |
| 3,455,940 | | 7/1969 | Stecker | 260/295 |
| 3,905,990 | | 9/1975 | Ehrmann et al. | 260/309.2 |
| 3,941,788 | | 3/1976 | Hankovsky et al. | 260/256.4 |
| 3,995,044 | * | 11/1976 | Kabbe et al. | 424/263 |
| 5,066,576 | | 11/1991 | Ichijima et al. | 430/558 |
| 5,296,339 | | 3/1994 | Fujita et al. | 430/389 |
| 5,789,428 | | 8/1998 | Shibata et al. | 514/367 |
| 5,877,195 | | 3/1999 | Lukenheimer et al. | 514/394 |

FOREIGN PATENT DOCUMENTS

| 0 598 962 | 6/1994 | (EP) . |
| 0 616 807 | 9/1994 | (EP) . |
| 0 882 718 | 12/1998 | (EP) . |
| 1 501 151 | 10/1966 | (FR) . |
| 7-133224 | 5/1995 | (JP) . |
| WO 96/00730 | 1/1996 | (WO) . |
| WO 96/33191 | 10/1996 | (WO) . |
| WO 96/33194 | 10/1996 | (WO) . |
| WO 96/39404 | 12/1996 | (WO) . |
| WO 97/11069 | 3/1997 | (WO) . |
| WO 97/24119 | 7/1997 | (WO) . |
| WO 98/17651 | 4/1998 | (WO) . |
| WO 98/45295 | 10/1998 | (WO) . |
| WO 99/37303 | 7/1999 | (WO) . |
| WO 99/47131 | 9/1999 | (WO) . |
| WO 99/47142 | 9/1999 | (WO) . |
| WO 99/47171 | 9/1999 | (WO) . |
| WO 00/59887 | 10/2000 | (WO) . |
| WO 00/59905 | 10/2000 | (WO) . |

OTHER PUBLICATIONS

V.M. Aruyzina et al., "The Synthesis of Substitution Products of 4H–Imidazo[5,1–b]Benzimidazole, V*. Some Substitution Reactions of 1,4,–Dimethyl and 1–Phenyl–4–Methylimidazo[5,1–b]Benzimidazoles", Chemistry of Heterocyclic Compounds, 1970, vol. 4, pp. 526–528.

V.M. Aruyzina et al., "Synthesis of 4H–Imidazo[5,1–a] Benzimidazole Substituents, VIII*, Synthesis of 1–Phenyl–4–Benzylimidazo[5,1–a]Benzimidazole and Some of Its 3–Substituents", Chemistry of Heterocyclic Compounds, No. 3, 1973, pp. 395–397.

Chemical Abstracts, vol. 73, No. 17, abstract No. 87845h. (Oct. 26, 1970).

Chemical Abstracts, vol. 127, No. 3, abstract No. 34242m, col. 650. (Jul. 21, 1997).

Cristos T.E. et al., "Corticotrophin–releasing factor receptor antagonists", Expert Opinion on Therapeutic Patents, vol. 8, No. 2, Feb. 1998 (1998–02), pp. 143–152, XP002109498.

* cited by examiner

Primary Examiner—Laura L. Stockton
(74) Attorney, Agent, or Firm—McDonnell Boehnen Hulbert & Berghoff; Steven J. Sarussi

(57) ABSTRACT

Disclosed are compounds of the forumla:

or the pharmaceutically acceptable non-toxic salts thereof wherein;

A is N or CH;

$R_1$ and $R_2$ represents hydrogen or lower alkyl;

G, $R_3$, $R_4$, $R_5$, $R_6$, $R_7$ and $R_8$ are variables defined herein.

These compounds are modulators of CRF receptors and are therefore useful for treating affective disorders, anxiety, depression, eating disorders, and stress disorders in humans and other animals. Methods of treatment of such disorders and well as packaged pharmaceutical compositions are also provided.

Compounds of the invention are also useful as probes for the localization of CRF receptors and as standards in assays for CRF receptor binding. Methods of using the compounds in receptor localization studies are given.

67 Claims, No Drawings

N-PHENYL BENZIMIDAZOLECARBOXAMIDE AND N-PHENYL INDOLECARBOXAMIDE DERIVATIVES

This application claims the benefit of U.S. Provisional Application no. 60/127,624, filed Apr. 1, 1999.

FIELD OF THE INVENTION

This invention relates N-phenyl benzimidazolecarboxamides and N-phenyl indolecarboxamides. When appropriately substituted, such compounds act as selective modulators of CRF1 receptors. This invention also relates to pharmaceutical compositions comprising such compounds and to the use of such compounds in treatment of psychiatric disorders and neurological diseases, including major depression, anxiety-related disorders, post-traumatic stress disorder, supranuclear palsy and feeding disorders, as well as treatment of immunological, cardiovascular or heart-related diseases and colonic hypersensitivity associated with psychopathological disturbance and stress. Additionally this invention relates to the use such compounds as probes for the localization of CRF1 receptors in cells and tissues.

BACKGROUND

Corticotropin releasing factor (CRF), a 41 amino acid peptide, is the primary physiological regulator of proopiomelanocortin (POMC) derived peptide secretion from the anterior pituitary gland. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain. There is also evidence that CRF plays a significant role in integrating the response of the immune system to physiological, psychological, and immunological stressors.

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system.

In affective disorder, or major depression, the concentration of CRF is significantly increased in the cerebral spinal fluid (CSF) of drug-free individuals. Furthermore, the density of CRF receptors is significantly decreased in the frontal cortex of suicide victims, consistent with a hypersecretion of CRF. In addition, there is a blunted adrenocorticotropin (ACTH) response to CRF (i.v. administered) observed in depressed patients. Preclinical studies in rats and non-human primates provide additional support for the hypothesis that hypersecretion of CRF may be involved in the symptoms seen in human depression. There is also preliminary evidence that tricyclic antidepressants can alter CRF levels and thus modulate the numbers of CRF receptors in brain.

CRF has also been implicated in the etiology of anxiety-related disorders. CRF produces anxiogenic effects in animals and interactions between benzodiazepine/non-benzodiazepine anxiolytics and CRF have been demonstrated in a variety of behavioral anxiety models. Preliminary studies using the putative CRF receptor antagonist α-helical ovine CRF (9-41) in a variety of behavioral paradigms demonstrate that the antagonist produces "anxiolytic-like" effects that are qualitatively similar to the benzodiazepines. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test and in the acoustic startle test in rats. The benzodiazepine receptor antagonist Ro 15-1788, which was without behavioral activity alone in the operant conflict test, reversed the effects of CRF in a dose-dependent manner, while the benzodiazepine inverse agonist FG 7142 enhanced the actions of CRF.

CRF has also been implicated in the pathogeneisis of certain immunological, cardiovascular or heart-related diseases such as hypertension, tachycardia and congestive heart failure, stroke and osteoporosis, as well as in premature birth, psychosocial dwarfism, stress-induced fever, ulcer, diarrhea, post-operative ileus and colonic hypersensitivity associated with psychopathological disturbance and stress.

The mechanisms and sites of action through which conventional anxiolytics and antidepressants produce their therapeutic effects remain to be fully elucidated. It has been hypothesized however, that they are involved in the suppression of CRF hypersecretion that is observed in these disorders. Of particular interest are that preliminary studies examining the effects of a CRF receptor antagonist peptide (α-helical $CRF_{9-41}$) in a variety of behavioral paradigms have demonstrated that the CRF antagonist produces "anxiolytic-like" effects qualitatively similar to the benzodiazepines.

SUMMARY OF THE INVENTION

The invention provides compounds of Formula I (shown below), and pharmaceutical compositions comprising compounds of Formula I. Such compounds bind to cell surface receptors, preferably G-coupled protein receptors, especially CRF receptors and most preferably CRF1 receptors. Preferred compounds of the invention exhibit high affinity for CRF 1 receptors. Additionally, preferred compounds of the invention also exhibit high specificity for CRF1 receptors.

Preferred compounds of the present invention exhibit activity as corticotropin releasing factor receptor antagonists and appear to suppress the anxiogenic effects of CRF hypersecretion. The invention also provides methods of using compounds of Formula I for the suppression of CRF hypersecretion and for the treatment of anxiogenic disorders.

The invention further comprises methods of treating patients suffering from certain disorders that are responsive to modulation of CRF1 receptors with an effective amount of a compound of the invention. These disorders include CNS disorders, particularly affective disorders, anxiety disorders, stress-related disorders, eating disorders and substance abuse. Treatment of human patients suffering from such disorders as well as other animals (domesticated companion animals (pets) or livestock animals in encompassed by the invention.

In another aspect, the invention provides pharmaceutical compositions comprising compounds of Formula I or the pharmaceutically acceptable salts or solvates thereof.

Additionally this invention relates to the use of the compounds of the invention (particularly labeled compounds of this invention) as probes for the localization of receptors in cells and tissues and as standards and reagents for use in determining the receptor-binding characteristics of test compounds. Labelled compounds of the invention may be used in in vitro studies such as is autoradiography of tissue sections or for in vivo methods, e.g. PET or SPECT scanning. Particularly, preferred compounds of the invention are useful as standards and reagents in determining the ability of a potential pharmaceutical to bind to the CRF1 receptor.

Accordingly, a broad aspect of the invention provides compounds of general Formula I:

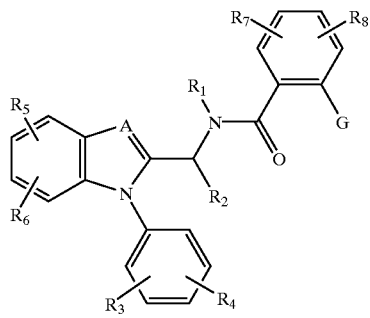

Formula I or the pharmaceutically acceptable non-toxic salts thereof wherein:

A represents N or C—Y, where Y is hydrogen or $(C_1-C_6)$ alkyl;

G represents hydrogen, halogen, trifluoromethyl, trifluoromethoxy, nitrile, $(C_1-C_6)$alkyl, $(C_1-C_6)$alkoxy, hydroxy, hydroxy$(C_1-C_6)$alkyl, $(C_1-C_6)$alkoxy $(C_1-C_6)$alkyl, —SH, $(C_1-C_6)$alkylthio–, thio$(C_1-C_6)$ alkyl or $(C_1-C_6)$alkyl thio$(C_1-C_6)$alkyl;

$R_1$ represents hydrogen, $(C_1-C_6)$alkyl, or hydroxy $(C_1-C_6)$alkyl;

$R_2$ represents hydrogen or $(C_1-C_6)$alkyl, with the proviso that $R_2$ is hydrogen when A is C—Y;

$R_3$ and $R_4$ are the same or different and represent hydrogen, halogen, trifluoromethyl, trifluoromethoxy, nitrile, $(C_1-C_6)$ alkyl, $(C_1-C_6)$alkoxy, hydroxy, hydroxy$(C_1-C_6)$alkyl, $(C_1-C_6)$ alkoxy$(C_1-C_6)$alkyl, —SH, $(C_1-C_6)$alkylthio, thio$(C_1-C_6)$ alkyl or $(C_1-C_6)$ alkyl thio$(C_1-C_6)$alkyl; and $R_5$, $R_6$, $R_7$ and $_8$ are the same or different and represent hydrogen, halogen, trifluoromethyl, trifluoromethoxy, nitrile, $(C_1-C_6)$alkyl, $(C_1-C_6)$alkoxy, $(C_1-C_6)$alkoxy $(C_1-C_6)$ alkoxy, hydroxy$(C_1-C_6)$alkoxy, hydroxy, hydroxy$(C_1-C_6)$ alkyl, $(C_1-C_6)$alkoxy$(C_1-C_6)$alkyl, —SH, amino, mono- or dialkylamino, $(C_1-C_6)$ alkylthio, thio$(C_1-C_6)$alkyl or $(C_1-C_6)$ alkyl thio$(C_1-C_6)$alkyl.

In another aspect, the invention provides methods for treating and/or preventing the above-listed disorders, which methods comprise administration to a patient of an effective amount of a compound of Formula I.

In yet another aspect, the invention provides intermediates useful in the preparation of the compounds of Formula I.

DETAILED DESCRIPTION OF THE INVENTION

Preferred compounds of Formula I

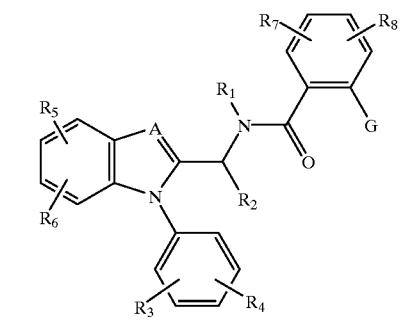

Formula I include those compounds, or the pharmaceutically acceptable non-toxic salts thereof wherein:

A represents N or C—Y, where Y is hydrogen or $(C_1-C_6)$ alkyl;

G represents halogen, trifluoromethyl, trifluoromethoxy, nitrile, $(C_1-C_6)$alkyl, $(C_1-C_6)$alkoxy, hydroxy, hydroxy $(C_1-C_6)$alkyl, $(C_1-C_6)$alkoxy$(C_1-C_6)$alkyl, —SH, $(C_1-C_6)$alkylthio-, thio$(C_1-C_6)$ alkyl or $(C_1-C_6)$alkyl thio$(C_1-C_6)$alkyl;

$R_1$ represents hydrogen, $(C_1-C_6)$alkyl or hydroxy$(C_1-C_6)$ alkyl;

$R_2$ represents hydrogen or $(C_1-C_6)$alkyl, with the proviso that $R_2$ is hydrogen when A is C—Y;

$R_3$ and $R_4$ are the same or different and represent hydrogen, halogen, trifluoromethyl, trifluoromethoxy, nitrile, $(C_1-C_6)$ alkyl, $(C_1-C_6)$alkoxy, $(C_1-C_6)$alkoxy $(C_1-C_6)$alkoxy, hydroxy$(C_1-C_6)$alkoxy, hydroxy, hydroxy$(C_1-C_6)$alkyl, $(C_1-C_6)$ alkoxy$(C_1-C_6)$alkyl, —SH, $(C_1-C_6)$alkylthio, thio$(C_1-C_6)$ alkyl or $(C_1-C_6)$ alkyl thio$(C_1-C_6)$alkyl, with the proviso that $R_3$ and $R_4$ cannot both be hydrogen simultaneously; and $R_5$, $R_6$, $R_7$ and $R_8$ are the same or different and represent hydrogen, halogen, trifluoromethyl, trifluoromethoxy, nitrile, $(C_1-C_6)$alkyl, $(C_1-C_6)$alkoxy, hydroxy, hydroxy $(C_1-C_6)$ alkyl, $(C_1-C_6)$alkoxy$(C_1-C_6)$alkyl, —SH, $(C_1-C_6)$alkylthio, thio$(C_1-C_6)$alkyl or $(C_1-C_6)$ alkyl thio$(C_1-C_6)$alkyl.

The compounds of the instant invention are represented by the general Formula I set forth above and include pharmaceutically acceptable non-toxic salts thereof.

Preferred compounds of Formula I are those where $R_1$ is a $C_1-C4$ group, more preferably a $C_2-C_4$ group, and most preferably an isopropyl group. Other preferred compounds of Formula I include those where $R_2$ is hydrogen or $C_1-C_3$ alkyl, preferably methyl. More preferred compounds of Formula I include those where $R_1$ is a $C_2-C_4$ group, most preferably an isopropyl group, and $R_2$ is hydrogen or $C_1-C_3$ alkyl, preferably methyl.

Particularly preferred compounds of Formula I are those where G is methyl and $R_7$ and $R_8$ are in the 4- and 6-positions on the phenyl ring respectively and independently represent hydrogen, $C_1-C_2$ alkoxy, $C_1-C_6$ alkyl, halogen, or trifluoromethyl.

Preferred

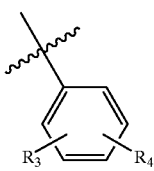

groups in Formula I include 2-, 3-, or 4-($C_1$–$C_6$) alkoxyphenyl, 4-($C_1$–$C_6$) alkoxy-2-($C_1$–$C_6$)alkylphenyl, 2-, 3-, or 4-($C_1$–$C_6$)al phenyl, 2- or 4-halophenyl, 4-hydroxyphenyl, and 4-hydroxy-2-($C_1$–$C_6$)alkylphenyl.

Particularly preferred

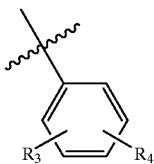

groups in Formula I include (4-methoxy-2-methylphenyl), 4-methoxyphenyl, 3-methoxyphenyl, 3-methylphenyl, 2-methoxyphenyl, 4-chloro-2-methylphenyl, 4-methylphenyl, 2-chlorophenyl, 4-fluorophenyl, 4-chlorophenyl, 4-hydroxyphenyl, 2,4-dimethylphenyl, 4-ethoxyphenyl, 4-hydroxy-2-methylphenyl, 3-hydroxy-4-methoxyphenyl.

In preferred compounds of Formula I, $R_5$, and $R_6$ are at the 5-and 6-positions of the benzimidazole or indole ring system and represent hydrogen, fluoro, chloro, bromo, $C_1$–$C_6$ alkoxy, more preferably methoxy or ethoxy, or $C_1$–$C_6$ alkyl, more preferably methyl or ethyl. Particularly preferred are compounds of Formula I where one of $R_5$ and $R_6$ is hydrogen and the other is hydrogen, fluoro, chloro, methoxy, ethoxy, methyl or ethyl.

Other preferred compounds of invention are encompassed by Formula II.

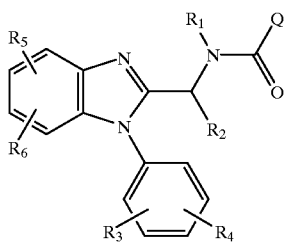

II wherein $R_1$ is as defined above for Formula I;

Q is

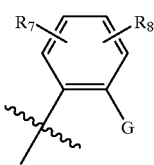

G represents halogen, trifluoromethyl, trifluoromethoxy, nitrile, ($C_1$–$C_6$)alkyl, ($C_1$–$C_6$) alkoxy, hydroxy, hydroxy($C_1$–$C_6$)alkyl, ($C_1$–$C_6$)alkoxy($C_1$–$C_6$)alkyl, —SH, ($C_1$–$C_6$)alkylthio, thio($C_1$–$C_6$) alkyl or ($C_1$–$C_6$) alkyl thio($C_1$–$C_6$)alkyl;

$R_2$ represents hydrogen or ($C_1$–$C_6$)alkyl, $R_3$ and $R_4$ are the same or different and represent hydrogen, halogen, trifluoromethyl, trifluoromethoxy, nitrile, ($C_1$–$C_6$) alkyl, ($C_1$–$C_6$)alkoxy, hydroxy, hydroxy($C_1$–$C_6$)alkyl, ($C_1$–$C_6$) alkoxy($C_1$–$C_6$)alkyl, thiol, ($C_1$–$C_6$)alkylthiol, thio($C_1$–$C_6$) alkyl or ($C_1$–$C_6$) alkyl thio($C_1$–$C_6$)alkyl, with the proviso that $R_3$ and $R_4$ cannot both be hydrogen; and $R_5$, $R_6$, $R_7$ and $R_8$, are the same or different and represent hydrogen, halogen, trifluoromethyl, trifluoromethoxy, nitrile, ($C_1$–$C_6$)alkyl, ($C_1$–$C_6$)alkoxy, hydroxy, hydroxy ($C_1$–$C_6$) alkyl, ($C_1$–$C_6$)alkoxy($C_1$–$C_6$)alkyl, thiol, ($C_1$–$C_6$) alkylthiol, thio($C_1$–$C_6$)alkyl or ($C_1$–$C_6$)alkyl thio($C_{1–20}$ $C_6$)alkyl.

Other preferred compounds of Formula II are those where $R_5$ and $R_6$ independently represent hydrogen, halogen, more preferably chloro or fluoro, hydroxy, trifluoromethyl, nitrile, $C_1$–$C_3$ alkyl, more preferably methyl, or $C_1$–$C_3$ alkoxy, more preferably methoxy or ethoxy.

Yet other preferred compounds of Formula II are those where G is $C_1$–$C_3$ alkyl, $C_1$–$C_3$ alkoxy, or halogen.

Still other preferred compounds of II include those where $R_5$ and $R_6$ are hydrogen and G is methyl, methoxy, or chloro. More preferred compounds of Formula II include those where $R_5$ and $R_6$ are hydrogen; G is methyl, methoxy, or chloro; and $R_7$ and $R_8$ are independently hydrogen, $C_1$–$C_6$ alkoxy, $C_1$–$C_6$ alkyl, halogen, or trifluoromethyl.

Particularly preferred compounds of Formula II are those where Q is

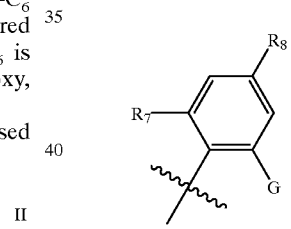

where G is $C_1$–$C_2$ alkyl and $R_7$ and $R_8$ are independently hydrogen, $C_1$–$C_2$ alkoxy, $C_1$–$C_2$ alkyl, halogen, or trifluoromethyl. Still other particularly preferred compounds of Formula II include those where $R_5$ and $R_6$ are hydrogen; G is methyl, methoxy, or chloro; and $R_7$ and $R_8$ are independently hydrogen, $C_1$–$C_6$ alkoxy, $C_1$–$C_6$ alkyl, halogen, or trifluoromethyl. In highly preferred embodiments of Formula II, Q is trimethylphenyl.

Other preferred compounds of Formula II include those where $R_1$ is $C_2$–$C_4$ alkyl, more preferably isopropyl. Yet other preferred compounds of Formula II include those where $R_2$ is hydrogen.

In other preferred compounds of Formula II, $R_5$ and $R_6$ are at the 5- and 6-positions of the benzimidazole or indole ring system and represent hydrogen, fluoro, chloro, bromo, $C_1$–$C_6$ alkoxy, more preferably methoxy or ethoxy, or $C_1$–$C_6$ alkyl, more preferably methyl or ethyl. Other more preferred are compounds of Formula II where one of $R_5$ and $R_6$ is hydrogen and the other is hydrogen, fluoro, chloro, methoxy, ethoxy, methyl or ethyl.

In addition, the invention encompasses compounds of Formula III

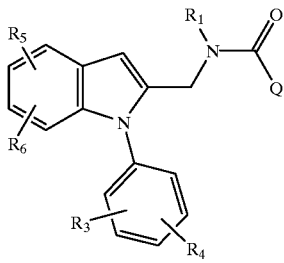

wherein $R_1$ is as defined above for Formula I. represents

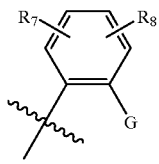

G represents halogen, trifluoromethyl, trifluoromethoxy, nitrile, $(C_1-C_6)$alkyl, $(C_1-C_6)$alkoxy, hydroxy, hydroxy $(C_1-C_6)$alkyl, $(C_1-C_6)$alkoxy$(C_1-C_6)$alkyl, —SH, $(C_1-C_6)$alkylthio, thio$(C_1-C_6)$ alkyl or $(C_1-C_6)$alkyl thio$(C_1-C_6)$alkyl;

$R_1$ represents hydrogen or $(C_1-C_6)$alkyl;

$R_3$ and $R_4$ are same or different and represent hydrogen, halogen, trifluoromethyl, trifluoromethoxy, nitrile, $(C_1-C_6)$ alkyl, $(C_1-C_6)$alkoxy, hydroxy, hydroxy $(C_1-C_6)$alkyl, $(C_1-C_6)$ alkoxy$(C_1-C_6)$alkyl, thio, $(C_1-C_6)$alkylthiol, thio$(C_1-C_6)$ alkyl or $(C_1-C_6)$alkyl thio$(C_1-C_6)$alkyl, with the proviso that $R_3$ and $R_4$ cannot both be hydrogen simultaneously; and $R_5$, $R_6$, $R_7$ and $R_8$ are the same or different and represent hydrogen, halogen, trifluoromethyl, trifluoromethoxy, nitrile, $(C_1-C_6)$alkyl, $(C_1-C_6)$alkoxy, hydroxy, hydroxy $(C_1-C_6)$ alkyl, $(C_1-C_6)$alkoxy$(C_1-C_6)$alkyl, —SH, $(C_1-C_6)$alkylthiol, thio$(C_1-C_6)$alkyl or $(C_1-C_6)$alkyl thio$(C_1-C_6)$alkyl.

Preferred compounds of Formula III are those where $R_5$ and $R_6$ independently represent hydrogen, halogen, more preferably chloro or fluoro, hydroxy, trifluoromethyl, nitrile, $C_1-C_3$ alkyl, more preferably methyl, or $C_1-C_3$ alkoxy, more preferably methoxy or ethoxy.

Yet other preferred compounds of Formula III are those where G is $C_1-C_3$ alkyl, $C_1-C_3$ alkoxy, or halogen.

Still other preferred compounds of III include those where $R_5$ and $R_6$ are hydrogen and G is methyl, methoxy, or chloro. More preferred compounds of Formula III include those where $R_5$ and $R_6$ are hydrogen; G is methyl, methoxy, or chloro; and $R_7$ and $R_8$ are independently hydrogen, $C_1-C_6$ alkoxy, $C_1-C_6$ alkyl, halogen, or trifluoromethyl.

Particularly preferred compounds of Formula III are those where Q is

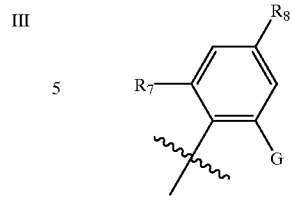

where G is $C_1-C_2$ alkyl and $R_7$ and $R_8$ are independently hydrogen, $C_1-C_2$ alkoxy, $C_1-C_2$ alkyl, halogen, or trifluoromethyl. Still other particularly preferred compounds of Formula III include those where $R_5$ and $R_6$ are hydrogen; G is methyl, methoxy, or chloro; and $R_7$ and $R_8$ are independently hydrogen, $C_1-C_6$ alkoxy, $C_1-C_6$ alkyl, halogen, or trifluoromethyl. In highly preferred embodiments of Formula III, Q is trimethylphenyl.

Other preferred compounds of Formula III include those where $R_1$ is $C_2-C_4$ alkyl, more preferably isopropyl.

In other preferred compounds of Formula III, $R_5$ and $R_6$ are at the 5- and 6-positions of the benzimidazole or indole ring system and represent hydrogen, fluoro, chloro, bromo, $C_1-C_6$ alkoxy, more preferably methoxy or ethoxy, or $C_1-C_6$ alkyl, more preferably methyl or ethyl. Other more preferred are compounds of Formula III where one of $R_5$ and $R_6$ is hydrogen and the other is hydrogen, fluoro, chloro, methoxy, ethoxy, methyl or ethyl.

Compounds of the invention are useful in treating a variety of conditions including affective disorders, anxiety disorders, stress disorders, eating disorders, and drug addiction.

Affective disorders include all types of depression, bipolar disorder, cyclothymia, and dysthymia.

Anxiety disorders include generalized anxiety disorder, panic, phobias and obsessive-compulsive disorder.

Stress-related disorders include post-traumatic stress disorder, hemorrhagic stress, stress-induced psychotic episodes, psychosocial dwarfism, stress headaches, stress-induced immune systems disorders such as stress-induced fever, and stress-related sleep disorders.

Eating disorders include anorexia nervosa, bulimia nervosa, and obesity.

Modulators of the CRF receptors may also be useful in the treatment of a variety of neurological disorders including supranuclear palsy, AIDS related dementias, multiinfarct dementia, neurodegenerative disorders such as Alzheimer's disease, Parkinson's disease, and Huntington's disease, head trauma, spinal cord trauma, ischemic neuronal damage, amyotrophic lateral sclerosis, disorders of pain perception such as fibromyalgia and epilepsy.

Additionally compounds of Formula I are useful as modulators of the CRF receptor in the treatment of a number of gastrointestestinal, cardiovascular, hormonal, autoimmune and inflammatory conditions. Such conditions include irritable bowel syndrome, ulcers, Crohn's disease, spastic colon, diarrhea, post operative ilius and colonic hypersensitivity associated with psychopathological disturbances or stress, hypertension, tachycardia, congestive heart failure, infertility, euthyroid sick syndrome, inflammatory conditions effected by rheumatoid arthritis and osteoarthritis, pain, asthma, psoriasis and allergies.

Compounds of Formula I are also useful as modulators of the $CRF_1$ receptor in the treatment of animal disorders associated with aberrant CRF levels. These conditions include porcine stress syndrome, bovine shipping fever, equine paroxysmal fibrillation, and dysfunctions induced by confinement in chickens, sheering stress in sheep or human-animal interaction related stress in dogs, psychosocial dwarfism and hypoglycemia.

By "alkyl", "lower alkyl", and "(C$_1$–C$_6$)alkyl" in the present invention is meant straight or branched chain alkyl groups or cycloalkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl, cyclopropyl, and cyclopropylmethyl.

By "alkoxy", "lower alkoxy", and "(C$_1$–C$_6$)alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By the term "halogen" in the present invention is meant fluorine, bromine, chlorine, and iodine.

Representative compound of the invention are shown below in Table 1

Table 1

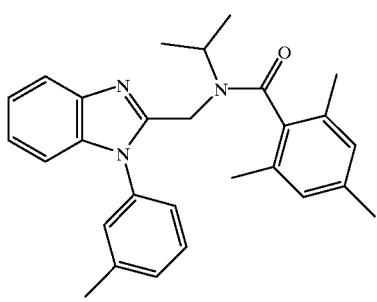

11

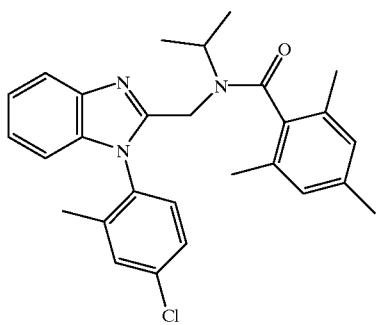

14

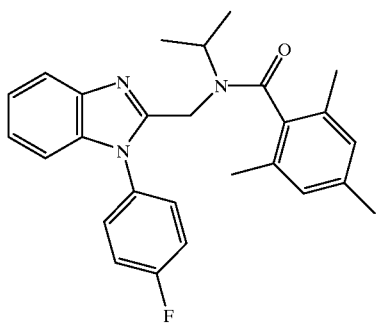

18

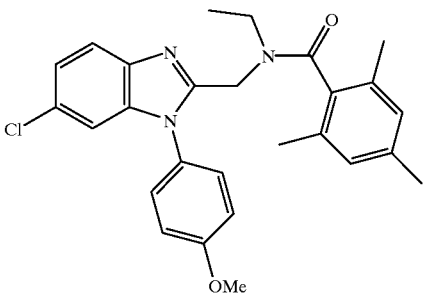

25

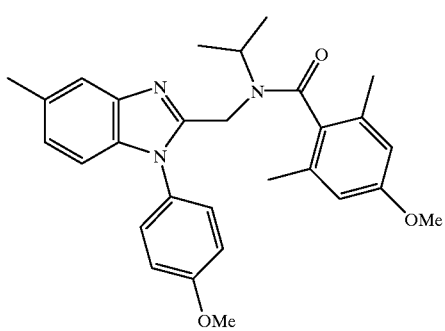

33

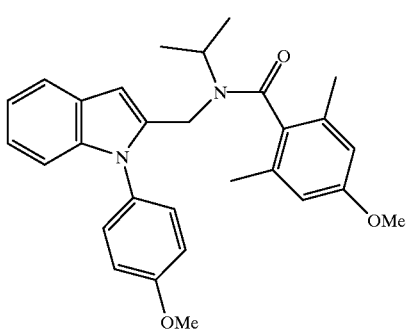

34

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds described in the Examples and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)n-COOH where n is 0–4, and the like. Those skilled in the art will recognize a wide variety of non-toxic pharmaceutically acceptable addition salts.

The present invention also encompasses acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

The invention encompasses all possible tautomers and rotamers of the compounds represented by Formula I.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Composition intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl disterate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most CNS disorders, a dosage regimen of 4 times daily or less is preferred. For the treatment of stress and depression a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

The present invention also pertains to packaged pharmaceutical compositions for treating disorders responsive to C5a receptor modulation, e.g., eating disorders, depression or stress. The packaged pharmaceutical compositions include a container holding a therapeutically effective amount of at least one CRF1 receptor modulator as described supra and instructions for using the treating disorder responsive to CRF1 receptor modulation in the patient.

Compounds of the invention can be prepared using the reactions depicted in Schemes I to III. In Schemes I–III, the groups G, $R_1$, $R_2$, $R_3$, $R_4$, $R_5$, $R_6$, $R_7$, $R_8$ and Y are as defined in general Formula I.

Scheme I

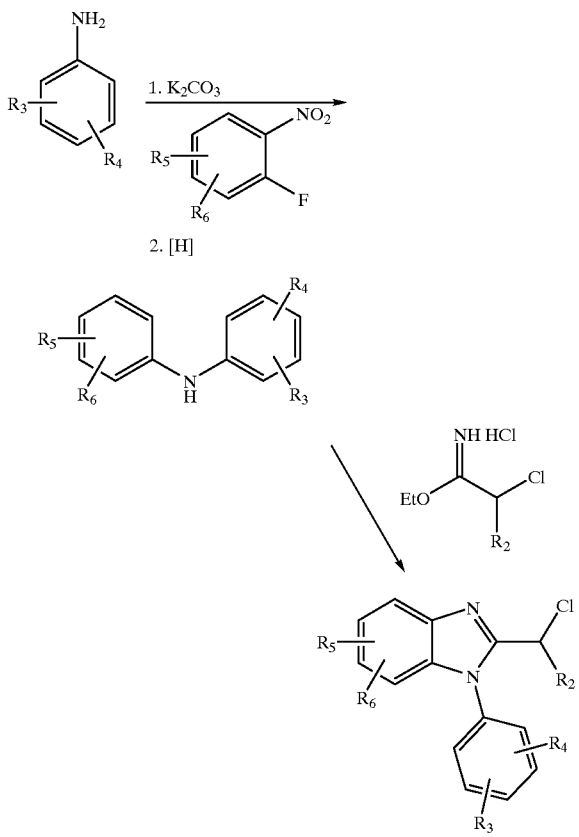

Scheme II

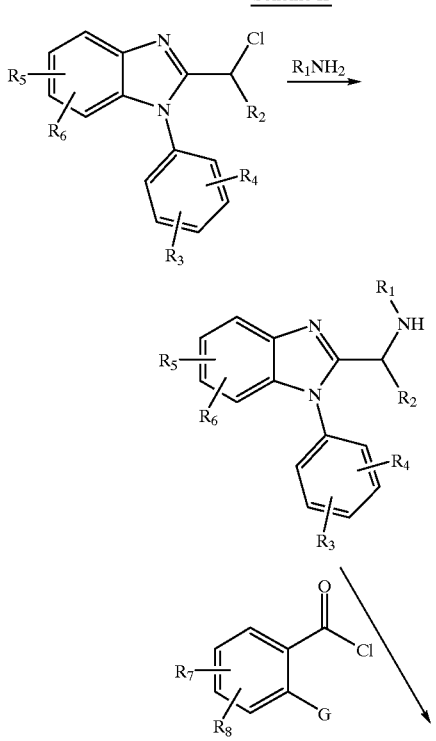

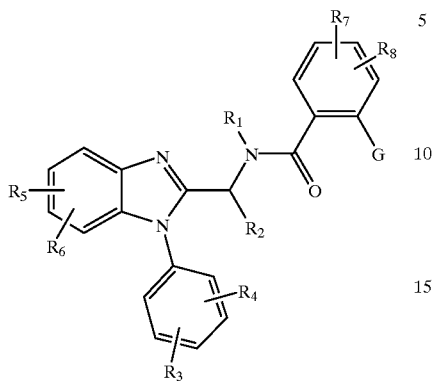

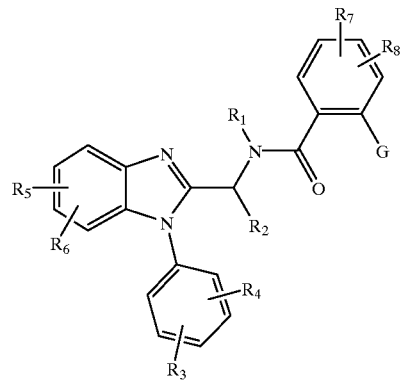

Those having skill in the art will recognize that the starting materials may be varied and additional steps employed to produce compounds encompassed by the present invention, as demonstrated by the following examples.

The disclosures of all articles and references mentioned in this application, including patents, are incorporated herein by reference.

The invention is illustrated further by the following examples which are not to be construed as limiting the invention in scope or spirit to the specific procedures described in them.

Commercial reagents were used without further purification. Room temperature refers to 20 to 25° C. TLC refers to thin layer chromatography. Mass spectral data were obtained either by ESI or APCI methods.

EXAMPLE 1

General Procedure for the Preparation of Chloromethylbenzimidazoles as Outlined in Scheme I 1. Imidate hydrochloride:

A solution of 150 mL (2.37 mole) of chloroacetonitrile, 139 mL (2.37 mole) of ethanol in 1,200 mL of dry benzene is cooled to 0° C. in an ice/ethanol bath. Dry HCl gas is bubbled through the vigorously stirred solution for approximately 30 minutes while the internal temperature is maintained below 10° C. The solution is allowed to stand at room temperature overnight. The resulting solid is filtered and washed with 2L of dry ether and allowed to air dry to afford 328 g (88%) of imidate hydrochloride.

2. 1-[2-(chloromethyl)benzimidazolyl]-4-methoxy-2-methylbenzene:

Scheme III

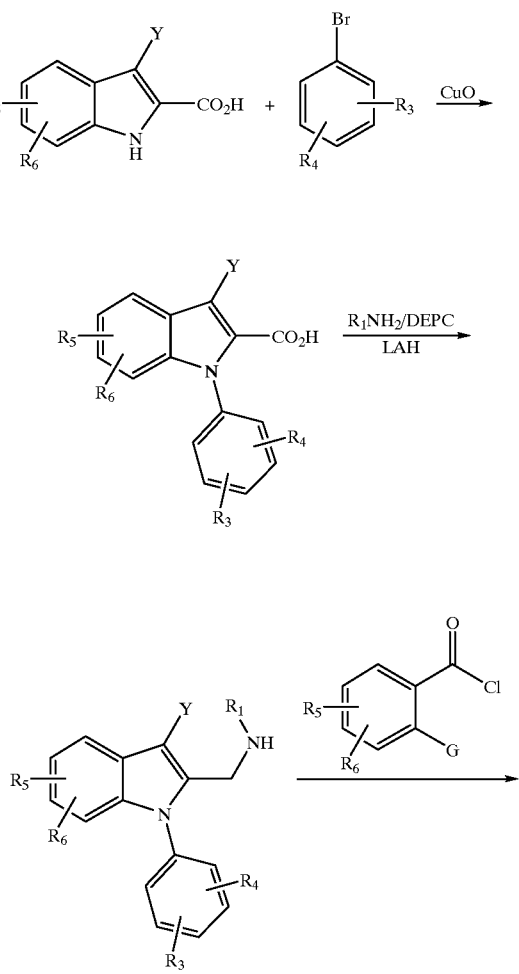

Diarylamines were prepared according to literature procedure [J. J. Kulagowski and C. W. Rees, *Synthesis*, 215 (1980)]. A solution of 60 g (0.26 mole) of (2-aminophenyl) (4-methoxy-2-methylphenyl) amine in 350 mL of anhydrous chloroform is treated with 59 g (0.37 mole) of imidate at room temperature. The heterogeneous reaction mixture is allowed to stir for 1 hour at room temperature at which time no starting material is detectable by TLC. 100 mL of saturated NaHCO$_3$ is added and extracted with 4 X 150 mL of CH$_2$Cl$_2$. The extracts are dried over anhydrous Na$_2$SO$_4$, the solvent removed in vacuo, and the residue chromatgraphed (SiO$_2$) with 20% ethyl acetate/hexane to afford 50 g (65%) of 1-[2-(chloromethyl)benzimidazolyl]-4-methoxy-2-methylbenzene: Mass Spec. 287 (M+H).

EXAMPLE 2

General Procedure for the Preparation of Benzimidazole Carboxamides as Shown in Scheme II
N-{[1-(4-methoxy-2-methylphenyl)benzimidazol-2-yl]methyl}-N-(methylethyl) (2,4,6-trimethylphenyl) carboxamide

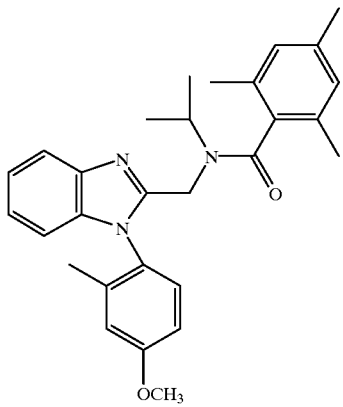

A solution of 3 g (10.5 mmole) 1-[2-(chloromethyl) benzimidazolyl]-4-methoxy-2-methylbenzene in 20 mL of dry acetonitrile is treated with 5 mL of isopropylamine for 1 hour in a sealed reaction vessel at 50° C. The solvent is removed in vacuo and the residue is partitioned between 30 mL of ethyl acetate and 10 mL of 1 N NaOH. The ethyl acetate layer is dried over anhydrous Na$_2$SO$_4$ and solvent removed in vacuo to afford 3.1 g (98%) {([1-(4-methoxy-2-methylphenyl)benzimidazol-2-yl]methyl}(methylethyl) amine. The latter amine is then vigorously stirred with 2.6 mL of 2,4,6-trimethylbenzoylchloride in a 1:1 mixture of dichloroethane and saturated aqueous sodium carbonate (30 mL) at room temperature for 1 hour. The mixture is partitioned, the organic layer is dried with Na$_2$SO$_4$ and the solvent removed in vacuo. The crystallized product is triturated in ethyl ether, filtered and dried to afford 4.4 g (92%) of white solid N-{[1-(4-methoxy-2-methylphenyl) benzimidazol-2-yl]methyl}-N-(methylethyl) (2,4,6-trimethylphenyl)carboxamide: Mass Spec. 456 (M+H); (Compound 1).

EXAMPLE 3

The following compounds are prepared essentially as described in Examples 1 and 2 and as shown in Schemes I and II.

a) N-{[1-(4-methoxyphenyl)benzimidazol-2-yl]methyl}-N-(methylethyl) (2,4,6-trichlorophenyl)carboxamide: MS 502 (M+H) (Compound 2).

b) N-{[1-(4-methoxyphenyl)benzimidazol-2-yl]methyl}-N-(methylethyl) (2-methylphenyl)carboxamide: MS 414 (M+H); (Compound 3).

c) N-{[1-(4-methoxyphenyl)benzimidazol-2-yl]methyl}-N-(methylethyl) (2,4-dimethylphenyl)carboxamide: MS 428 (M+H); (Compound 4).

d) N-{[1-(4-methoxyphenyl)benzimidazol-2-yl]methyl}-N-(methylethyl) (2-methoxyphenyl)carboxamide: MS 430 (M+H); (Compound 5).

e) N-{[1-(4-methoxyphenyl)benzimidazol-2-yl]methyl}-N-(methylethyl) (3-fluoro-2-methylphenyl)carboxamide: MS 432 (M+H); (Compound 6).

f) N-{[1-(4-methoxyphenyl)benzimidazol-2-yl]methyl}-N-(methylethyl) (4-chloro-2-methoxyphenyl)carboxamide: MS 464 (M+H); (Compound 7).

g) N-{[1-(4-methoxyphenyl)benzimidazol-2-yl]methyl}-N-(methylethyl) (2,4-dichlorophenyl)carboxamide: MS 468 (M+H); (Compound 8).

h) N-{[1-(4-methoxyphenyl)benzimidazol-2-yl]methyl}-N-(methylethyl) (2,6-dimethylphenyl)carboxamide: MS 428 (M+H); (Compound 9).

i) N-{[1-(3-methoxyphenyl)benzimidazol-2-yl]methyl}-N-(methylethyl) (2,4,6-trimethylphenyl)carboxamide: MS 442 (M+H); (Compound 10).

j) N-{[1-(3-methylphenyl)benzimidazol-2-yl]methyl}-N-(methylethyl) (2,4,6-trimethylphenyl)carboxamide: MS 426 (M+H); (Compound 11).

k) N-{[1-(2-methoxyphenyl)benzimidazol-2-yl]methyl}-N-(methylethyl) (2,4,6-trimethylphenyl)carboxamide: MS 442 (M+H); (Compound 12).

l) N-{[1-(2-methylphenyl)benzimidazol-2-yl]methyl}-N-(methylethyl) (2,4,6-trimethylphenyl)carboxamide: MS 426 (M+H) (Compound 13).

m) N-{[1-(4-chloro-2-methylphenyl)benzimidazol-2-yl]methyl}-N-(methylethyl) (2,4,6-trimethylphenyl) carboxamide: MS 461 (M+H); (Compound 14).

n) N-{[1-(4-methylphenyl)benzimidazol-2-yl]methyl}-N-(methylethyl) (2,4,6-trimethylphenyl)carboxamide: MS 426 (M+H) (Compound 15).

o) N-{[1-(4-methoxyphenyl)benzimidazol-2-yl]methyl}-N-(methylethyl) (2,4,6-trimethylphenyl)carboxamide: MS 442 (M+H); (Compound 16).

p) N-{[1-(2-chlorophenyl)benzimidazol-2-yl]methyl}-N-(methylethyl) (2,4,6-trimethylphenyl)carboxamide: MS 446 (M+H); (Compound 17).

q) N-{[1-(4-fluorophenyl)benzimidazol-2-yl]methyl}-N-(methylethyl) (2,4,6-trimethylphenyl)carboxamide: MS 430 (M+H) (Compound 18).

r) N-{[1-(4-chlorophenyl)benzimidazol-2-yl]methyl}-N-(methylethyl) (2,4,6-trimethylphenyl)carboxamide: MS 446 (M+H); (Compound 19).

s) N-{[1-(4-methoxyphenyl)benzimidazol-2-yl]methyl}-N-(methylethyl) (2-fluoro-4-trifluoromethylphenyl) carboxamide: MS 486 (M+H); (Compound 20).

t) N-{[1-(4-hydroxyphenyl)benzimidazol-2-yl]methyl}-N-(methylethyl) (2,4,6-trimethylphenyl)carboxamide: MS 428 (M+H) (Compound 21).

u) N-{[5-fluoro-1-(4-methoxyphenyl)benzimidazol-2-yl] methyl}-N-(methylethyl) (2,4,6-trimethylphenyl) carboxamide: MS 460 (M+H); (Compound 22).

v) N-{[6-methoxy-1-(4-methoxyphenyl)benzimidazol-2-yl]methyl}-N-(methylethyl) (2,4,6-trimethylphenyl) carboxamide: MS 472 (M+H); (Compound 23).

w) N-{[6-ethoxy-1-(4-methoxyphenyl)benzimidazol-2-yl]methyl}-N-(methylethyl) (2,4,6-trimethylphenyl)carboxamide: MS 486 (M+H); (Compound 24).

x) N-{[6-chloro-1-(4-methoxyphenyl)benzimidazol-2-yl]methyl}-N-(methylethyl) (2,4,6-trimethylphenyl)carboxamide: MS 477 (M+H); (Compound 25).

y) N-{[1-(4-methoxyphenyl)-5-methylbenzimidazol-2-yl]methyl}-N-(methylethyl) (2,4,6-trimethylphenyl)carboxamide: MS 456 (M+H); (Compound 26).

z) N-{[1-(2,4-dimethylphenyl)benzimidazol-2-yl]methyl}-N-(methylethyl) (2,4,6-trimethylphenyl)carboxamide: MS 440 (M+H) (Compound 27).

aa) N-{[1-(4-ethoxyphenyl)benzimidazol-2-y]methyl}-N-(methylethyl) (2, 4, 6-trimethylphenyl)carboxamide: MS 456 (M+H) (Compound 28).

bb) N-{[1-(4-hydroxy-2-methylphenyl)benzimidazol-2-yl]methyl}-N-(methylethyl) (2,4,6-trimethylphenyl)carboxamide: MS 442 (M+H); (Compound 29).

cc) N-{[1-(3-hydroxy-4-methoxyphenyl)benzimidazol-2-yl]methyl}-N-(methylethyl) (2,4,6-trimethylphenyl)carboxamide: MS 458 (M+H); (Compound 30).

dd) N-{[1-(4-methoxyphenyl)benzimidazol-2-yl]methyl}-N-(methylethyl) (2,6-dimethyl-4-methoxyphenyl)carboxamide: MS 458 (M+H); (Compound 31).

ee) N-{[5-fluoro-1-(4-methoxyphenyl)benzimidazol-2-yl]methyl}-N-(methylethyl) (2,6-dimethyl-4-methoxyphenyl)carboxamide: MS 476 (M+H); (Compound 32).

ff) N-{[1-(4-methoxyphenyl)-5-methylbenzimidazol-2-yl]methyl}-N-(methylethyl) (2,6-dimethyl-4-methoxyphenyl)carboxamide: MS 472 (M+H); (Compound 33).

gg) N-[(1-phenylbenzimidazol-2-yl)methyl]-N-(methylethyl) (2,4,6-trimethylphenyl)carboxamide: MS 412 (M+H); (Compound 34).

hh) N-[(1-phenylbenzimidazol-2-yl)methyl]-N-(methylethyl) (2,4,6-trichlorophenyl)carboxamide: MS 472 (M+H); (Compound 35).

ii) N-[(1-phenylbenzimidazol-2-yl)methyl]-N-(methylethyl) (2,4-dimethylphenyl)carboxamide: MS 398 (M+H); (Compound 36).

jj) N-{[1-(2,4,6-trimethylphenyl)benzimidazol-2-yl]methyl}-N-(methylethyl) (2,4,6-trimethylphenyl)carboxamide: MS 454 (M+H); (Compound 37).

kk) N-{[1-(2,4,6-trimethylphenyl)benzimidazol-2-yl]methyl}-N-(cyclopropyl) (2,4,6-trimethylphenyl)carboxamide: MS 452 (M+H); (Compound 38).

ll) N-[(1-phenylbenzimidazol-2-yl)methyl]-N-(cyclopropyl) (2, 4-dimethylphenyl)carboxamide: MS 410 (M+H); (Compound 39).

mm) N-{[1-(4-methoxyphenyl)benzimidazol-2-yl]methyl}-N-(methylethyl) (4-trifluoromethylphenyl)carboxamide: MS 466 (M+H); (Compound 40).

nn) N-{[1-(4-methoxyphenyl)benzimidazol-2-yl]methyl}-N-(dimethylethyl) (2,4,6-trimethylphenyl)carboxamide: MS 456 (M+H); (Compound 41)

oo) N-{[1-(4-methoxyphenyl)benzimidazol-2-yl]methyl} (2,4,6-trimethylphenyl) carboxamide: MS 400 (M+H); (Compound 42).

pp) N-{[1-(4-(2-hydroxyethoxy)phenyl)benzimidazol-2-yl]methyl}-N-(methylethyl) (2,4,6-trimethylphenyl)carboxamide: MS 472 (M+H); (Compound 43).

qq) N-{[6-hydroxy-1-(4-methoxyphenyl)benzimidazol-2-yl]methyl}-N-(methylethyl) (2,4,6-trimethylphenyl)carboxamide: MS 458 (M+H); (Compound 44).

rr) N-{[6-chloro-1-(4-methoxyphenyl)benzimidazol-2-yl]methyl}-N-(methylethyl) (2,6-dimethyl-4-methoxyphenyl)carboxamide: MS 492 (M+H); (Compound 45).

ss) N-{[1-(4-methoxyphenyl)benzimidazol-2-yl]methyl}-N-(methylethyl) (4-chloro-2,6-dimethylphenyl)carboxamide: MS 462 (M+H); (Compound 46).

tt) N-{[5-methyl-1-(4-methoxyphenyl)benzimidazol-2-yl]methyl}-N-(methylethyl) (4-chloro-2,6-dimethylphenyl)carboxamide: MS 476 (M+H); (Compound 47).

uu) N-{[5-methyl-1-(4-methoxyphenyl)benzimidazol-2-yl]methyl}-N-(methylethyl) (4-methoxy-2-methylphenyl)carboxamide: MS 458 (M+H); (Compound 48).

vv) N-{[5-bromo-1-(4-methoxyphenyl)benzimidazol-2-yl]methyl}-N-(methylethyl) (2,4,6-trimethylphenyl)carboxamide: MS 520 (M+H); (Compound 49).

ww) N-{[1-(4-fluoro-2-methylphenyl)benzimidazol-2-yl]methyl}-N-(methylethyl) (2,4,6-trimethylphenyl)carboxamide: MS 444 (M+H); (Compound 50).

xx) N-{[1-(4-methoxy-2-methylphenyl)-5-trifluoromethylbenzimidazol-2-yl]methyl}-N-(methylethyl) (2,4,6-trimethylphenyl)carboxamide: MS 524 (M+H); (Compound 51).

yy) N-{[5-tert-butoxycarbamyl-1-(4-methoxyphenyl)benzimidazol-2-yl]methyl}-N-(methylethyl) (2,4,6-trimethylphenyl)carboxamide: MS 557 (M+H); (Compound 52).

zz) N-{[5-amino-1-(4-methoxyphenyl)benzimidazol-2-yl]methyl}-N-(methylethyl) (2,4,6-trimethylphenyl)carboxamide: MS 457 (M+H); (Compound 53).

aaa) N-{[5-dimethylamino-1-(4-methoxyphenyl)benzimidazol-2-yl]methyl}-N-(methylethyl) (2,4,6-trimethylphenyl)carboxamide: MS 485 (M+H); (Compound 54).

bbb) N-{[5-methyl-1-(4-trifluoromethylphenyl)benzimidazol-2-yl]methyl}-N-(methylethyl) (2,4,6-trimethylphenyl)carboxamide: MS 494 (M+H); (Compound 55).

ccc) N-{[5-methyl-1-(4-trifluoromethylphenyl)benzimidazol-2-yl]methyl}-N-(methylethyl) (4-chloro-2,6-dimethylphenyl)carboxamide: MS 514 (M+H); (Compound 56).

ddd) N-{[1-(4-hydroxy-2-methylphenyl)-5-trifluoromethyl benzimidazol-2-yl]methyl}-N-(methylethyl)(2,4,6-trimethylphenyl)carboxamide: MS 510 (M+H); (Compound 57).

eee) N-{[1-(4-(2-hydroxyethoxy)-2-methylphenyl)-5-trifluoromethylbenzimidazol-2-yl ]methyl}-N-(methylethyl)(2,4,6-trimethylphenyl)carboxamide: MS 554 (M+H); (Compound 58).

fff) N-{[1(4-methoxyphenyl)-5-trifluoromethylbenzimidazol-2-yl]methyl}-N-(methylethyl) (4-dimethylamino-2,6-dimethylphenyl)carboxamide: MS 539 (M+H); (Compound 59).

ggg) N-{[1-(4-methoxyphenyl)-5-trifluoromethylbenzimidazol-2-yl]methyl}-N-(methylethyl) (4-hydroxy-2,6-dimethylphenyl)carboxamide: MS 512 (M+H); (Compound 60).

hhh) N-{[5-diethylamino-1-(4-methoxyphenyl)benzimidazol-2-yl]methyl}-N-(methylethyl) (2,4,6-trimethylphenyl)carboxamide: MS 513 (M+H); (Compound 61).

iii) N-{[1-(4-(2-hydroxyethoxy)-2-methylphenyl)benzimidazol-2-yl]methyl}-N-(methylethyl) (2,4,6-trimethylphenyl)carboxamide: MS 486 (M+H); (Compound 62).

jjj) N-{[1-(4-methoxyphenyl)-5-trifluoromethylbenzimidazol-2-yl]methyl}-N-[1-(hydroxymethyl) ethyl](2,4,6-trimethylphenyl)carboxamide: MS 526 (M+H); (Compound 63).

kkk) N-{[1-(4-methoxyphenyl)-5-trifluoromethyl benzimidazol-2-yl]methyl}-N-(3-hydroxypropyl) (2,4,6-trimethylphenyl)carboxamide: MS 526 (M+H); (Compound 64).

lll) N-{[1-(4-methoxyphenyl)-5-trifluoromethyl benzimidazol-2-yl]methyl}-N-[2-hydroxy-1-(hydroxymethyl) ethyl](2,4,6-trimethylphenyl)carboxamide: MS 542 (M+H); (Compound 65).

mmm) N-{[(5-iodo-1-(4-methoxyphenyl)benzimidazol-2-yl]methyl}-N-(methylethyl) (2,4,6-trimethylphenyl)carboxamide: MS 568 (M+H); (Compound 66).

nnn) N-{[1-(4-hydroxyphenyl)-5-trifluoromethyl benzimidazol-2-yl]methyl}-N-(methylethyl) (2,4,6-trimethylphenyl)carboxamide: MS 496 (M+H); (Compound 67).

EXAMPLE 4

General Procedure for the Preparation of Indole Carboxamides as Shown in Scheme III
N-{[1-(4-methoxyphenyl)indol-2-yl]methyl}-N-(methylethyl)(2,4,6-trimethylphenyl)carboxamide

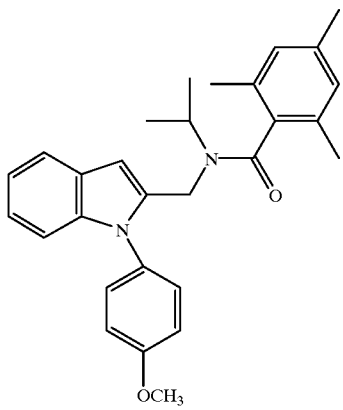

N-Phenyl indolecarboxylic acids are prepared according to literature procedures [P.C. Unangst et al., *J. Heterocyclic Chem.*, 24, 811 (1987)]. To a solution of the N-(4-methoxy)phenylindole-2-carboxylic acid (2 g, 7.48 mmol) in N,N-dimethylformamide (15 ml) is added triethylamine (1.25 ml, 9 mmol) followed by diethyl cyanophosphonate (DECP) (1.52 ml, 9 mmol) at 0° C. The resulting solution is stirred for 10 minutes before isopropylamine (1.92 ml, 22.5 mmol) is added. After stirring at room temperature for 1 hour, the solution is diluted with water and extracted with ethyl acetate. The extracts are combined, washed with water, washed with brine and then dried. Solvent is removed in vacuo to give the product as a light yellow solid (2.07 g, 90%).

A mixture of the latter amide (840 mg, 2.72 mmol) in tetrahydrofuran (THF, 4 mL) is added to a solution of lithium aluminum hydride in THF (1N, 6.8 ml). The resulting yellow solution is refluxed for 24 hours and then cooled to room temperature, diluted with $Et_2O$ and quenched by adding water at 0° C. until formation of a gel. The $Et_2O$ layer is separated and the gel is extracted with more $Et_2O$. The combined $Et_2O$ extract is washed with water, washed with brine and dried. Solvent is removed in vacuo to give a yellow oil residue that is stirred in 1N HCl (5 ml) and $Et_2O$ (10 ml). The white precipitate is separated, washed with water, rinsed with $Et_2O$ and dried to give the product as its hydrochloride (430 mg, 48%).

To the latter amine (165 mg, 0.5 mmol) in dichloroethane (2 ml) and triethylamine (0.25 ml, 1.75 mmol) is added 2,4,6-trimethylbenzoyl chloride (0.166 ml, 1 mmol). The resulting mixture is stirred at room temperature for 4 hours, diluted with $CH_2Cl_2$, washed with water, washed with saturated aqueous $NaHCO_3$ solution, washed with brine and dried. The solvent is removed in vacuo and the residue is purified by silica gel column ($CH_2Cl_2$ elution) to give a white solid (100 mg) of N-{[1-(4-methoxyphenyl) indol-2-yl]methyl}-N-(methylethyl)$_{2,4,6}$-trimethylphenyl) carboxamide: MS 441 (M+H); (Compound 68).

EXAMPLE 5

Assay for CRF Receptor Binding Activity

The following two assays for human CRF1 receptor activity are standard assays of CRF binding that may be used to determine the affinity of CRF for the CRF receptor.
Assay for Recombinant Human $CRF_1$ Receptor Binding Activity CRF receptor binding is performed using a modified version of the assay described by Grigoriadis and De Souza (*Methods in Neurosciences*, Vol. 5, 1991). Membrane pellets containing CRF receptors are re-suspended in 50 mM Tris buffer pH 7.7 containing 10 mM $MgCl_2$ and 2 mM EDTA and centrifuged for 10 minutes at 48000 g. Membranes are washed again and brought to a final concentration of 1500 mg/ml in binding buffer (Tris buffer above with 0.1% BSA, 15 mM bacitracin and 0.01 mg/mL aprotinin.). For the binding assay, 100 mL of the membrane preparation is added to 96 well microtube plates containing 100 mL of $^{125}$I-CRF (SA 2200 Ci/mmol, final concentration of 100 pM) and 50 mL of drug. Binding is carried out at room temperature for 2 hours. Plates are then harvested on a Brandel 96 well cell harvester and filters are counted for gamma emissions on a Wallac 1205 Betaplate liquid scintillation counter. Non specific binding is defined by 1 mM cold CRF. $IC_{50}$ values are calculated with the non-linear curve fitting program RS/1 (BBN Software Products Corp., Cambridge, Mass.). The binding affinity for the compounds of Formula I expressed as $IC_{50}$ value, generally ranges from about 0.5 nanomolar to about 10 micromolar.

Preferred Arylpyrimidines of the invention exhibit good activity in standard in vitro receptor binding assays, specifically the assay as specified in Example 44, which follows and is defined below. Particularly preferred arylpyrimidines of the invention have an $IC_{50}$ of about 10 micromolar or less, still more preferably and $IC_{50}$ of about 100 nanomolar or less even more preferably an $IC_{50}$ of about 10 nanomolar or less or even 1 nanomolare or less in such a defined standard in vitro CRF receptor binding assay.

Alternatively, the binding activity of the compounds of formula I to the human $CRF_1$ receptor can be measured as follows:
Assay for Human CRF Receptor Binding Activity in IMR32 cells IMR-32 human neuroblastoma cells are grown to 80% confluence in EMEM containing Earle's Balanced Salts and 2 mM 1-glutamine with 10% FBS, 25 mM HEPES, 1 mM Sodium Pyruvate, and nonessential amino acids. At this time, flasks of cells are treated with 2.5 uM 5-bromo-2'-deoxyuridine (Br-dU) for 10 days. Media is changed every 3–4 days across the 10-day period. Cells are harvested using No-Zyme (JRH Biosciences) and rinsed with PBS. For membrane preparation, cells are homogenized in wash buffer (50 mM Tris HCl, 10 mM $MgCl_2$, 2 mM EGTA, pH 7.4) and centrifuged at 48,000×g for 10 minutes at 4° C. Pellets are resuspended, homogenized and centrifuged two additional times. The receptor binding assay is performed using assay buffer (50 mM Tris HCl, 10 mM $MgCl_2$, 2 mM EGTA, pH 7.4, 0.1% BSA, 0.1 mM bacitracin (22.0 mg/100 mL)), 150 ug protein/tube, and [$^{125}$I] Sauvagine (NEN; 100 pM for competition analysis and 10 pM-1 nM for saturation analysis) to yield a final volume of 200 uL. Nonspecific binding is defined using 2 uM r/h CRF or 9–41 alpha-helical CRF. Cells are incubated for 2 hours at room temperature. The assay is terminated by rapid vacuum filtration (Tomtec: Deepwell 3) through GFC filters presoaked in 1% PEI using ice-cold 50 mM Tris Hcl and dry thoroughly by air. Specific Binding: 70–80%; Kd (nM): 0.30 nM; Bmax (fmole/mg protein): 40–50. $IC_{50}$ values are calculated with the non-linear curve fitting program RS/1 (BBN Software Products Corp., Cambridge, Mass.). The binding affinities for the compounds of Formula I expressed as $IC_{50}$ value are less than 10 micromolar.

EXAMPLE 6

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE 7

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

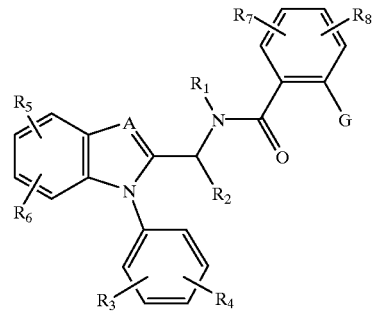

or a pharmaceutically acceptable non-toxic salt thereof wherein:

A represents N;

G represents halogen, trifluoromethyl, trifluoromethoxy, cyano, ($C_1$–$C_6$)alkyl, ($C_1$–$C_6$)alkoxy, hydroxy, hydroxy ($C_1$–$C_6$) alkyl, ($C_1$–$C_6$)alkoxy($C_1$–$C_6$)alkyl, —SH, ($C_1$–$C_6$)alkylthio-, thio ($C_1$–$C_6$)alkyl or ($C_1$–$C_6$)alkyl thio($C_1$–$C_6$)alkyl;

$R_1$ represents hydrogen, ($C_1$–$C_6$)alkyl, or hydroxy ($C_1$–$C_6$)alkyl;

$R_2$ represents hydrogen or ($C_1$–$C_6$)alkyl; and $R_3$, and $R_4$ are the same or different and represent hydrogen, halogen, trifluoromethyl, trifluoromethoxy, cyano, ($C_1$–$C_6$)alkyl, ($C_1$–$C_6$)alkoxy, hydroxy, hydroxy ($C_1$–$C_6$)alkyl, ($C_1$–$C_6$)alkoxy($C_1$–$C_6$)alkyl, —SH, ($C_1$–$C_6$)alkylthio, thio($C_1$-$C_6$) alkyl or ($C_1$–$C_6$)alkyl thio($C_1$–$C_6$)alkyl;

$R_5$, $R_6$, $R_7$ and $R_8$ are the same or different and represent hydrogen, halogen, trifluoromethyl, trifluoromethoxy, cyano, ($C_1$–$C_6$)alkyl, ($C_1$–$C_6$)alkoxy, ($C_1$–$C_6$)alkoxy ($C_1$–$C_6$)alkoxy, hydroxy($C_1$–$C_6$)alkoxy, hydroxy, hydroxy($C_1$–$C_6$)alkyl, ($C_1$-$C_6$) alkoxy($C_1$–$C_6$)alkyl, —SH, ($C_1$–$C_6$)alkylthio, thio($C_1$–$C_6$)alkyl or ($C_1$–$C_6$) alkyl thio($C_1$–$C_6$)alkyl.

2. A compound of the formula:

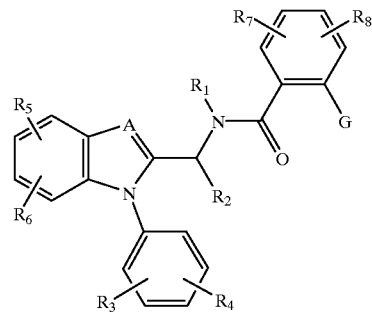

or a pharmaceutically acceptable non-toxic salt thereof wherein:

A represents N;

G represents halogen, trifluoromethyl, trifluoromethoxy, cyano, ($C_1$–$C_6$)alkyl, ($C_1$–$C_6$)alkoxy, hydroxy, hydroxy ($C_1$-$C_6$) alkyl, ($C_1$–$C_6$)alkoxy($C_1$–$C_6$)alkyl, —SH, ($C_1$–$C_6$)alkylthio-, thio($C_1$–$C_6$)alkyl or ($C_1$–$C_6$)alkyl thio($C_1$–$C_6$)alkyl;

$R_1$ represents hydrogen, ($C_1$–$C_6$)alkyl or hydroxy($C_1$–$C_6$) alkyl;

$R_2$ represents hydrogen or ($C_1$–$C_6$)alkyl;

$R_3$ and $R_4$ are the same or different and represent hydrogen, halogen, trifluoromethyl, trifluoromethoxy, cyano, ($C_1$–$C_6$)alkyl, ($C_1$–$C_6$)alkoxy, ($C_1$–$C_6$)alkoxy ($C_1$–$C_6$)alkoxy, hydroxy($C_1$–$C_6$)alkoxy, hydroxy, hydroxy($C_1$–$C_6$)alkyl, ($C_1$-$C_6$) alkoxy($C_1$–$C_6$)alkyl, —SH, ($C_1$–$C_6$)alkylthio, thio($C_1$–$C_6$)alkyl or ($C_1$–$C_6$) alkyl thio($C_1$–$C_6$)alkyl, with the proviso that $R_3$ and $R_4$ cannot both be hydrogen simultaneously; and $R_5$, $R_6$, $R_7$ and $R_8$ are the same or different and represent hydrogen, halogen, trifluoromethyl, trifluoromethoxy, cyano, ($C_1$–$C_6$)alkyl, ($C_1$–$C_6$)alkoxy, ($C_1$–$C_6$)alkoxy ($C_1$–$C_6$)alkoxy, hydroxy($C_1$–$C_6$)alkoxy, hydroxy, hydroxy($C_1$–$C_6$)alkyl, ($C_1$-$C_6$) alkoxy($C_1$–$C_6$)alkyl, —SH, ($C_1$–$C_6$)alkylthio, thio($C_1$–$C_6$)alkyl or ($C_1$–$C_6$) alkyl thio($C_1$–$C_6$)alkyl.

3. A compound of the formula:

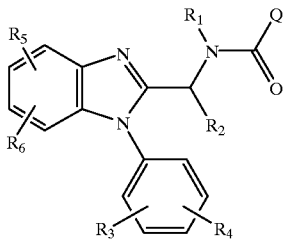

or a pharmaceutically acceptable non-toxic salt thereof wherein:

Q represents

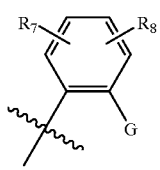

G represents halogen, trifluoromethyl, trifluoromethoxy, cyano, ($C_1$–$C_6$)alkyl, ($C_1$–$C_6$)alkoxy, hydroxy, hydroxy ($C_1$–$C_6$) alkyl, ($C_1$–$C_6$)alkoxy($C_1$–$C_6$)alkyl, —SH, ($C_1$–$C_6$)alkylthio, thio($C_1$–$C_6$)alkyl or ($C_1$–$C_6$)alkyl thio($C_1$–$C_6$)alkyl;

$R_1$ represents hydrogen or ($C_1$–$C_6$)alkyl;

$R_2$ represents hydrogen or ($C_1$–$C_6$)alkyl;

$R_3$ and $R_4$ are the same or different and represent hydrogen, halogen, trifluoromethyl, trifluoromethoxy, cyano, ($C_1$–$C_6$)alkyl, ($C_1$–$C_6$)alkoxy, hydroxy, hydroxy ($C_1$–$C_6$)alkyl, ($C_1$–$C_6$)alkoxy($C_1$–$C_6$)alkyl, thiol, ($C_1$–$C_6$)alkylthiol, thio($C_1$-$C_6$) alkyl or ($C_1$–$C_6$)alkyl thio($C_1$–$C_6$)alkyl, with the proviso that $R_3$ and $R_4$ cannot both be hydrogen; and $R_5$, $R_6$, $R_7$ and $R_8$ are the same or different and represent hydrogen, halogen, trifluoromethyl, trifluoromethoxy, nitrile, ($C_1$–$C_6$) alkyl, ($C_1$–$C_6$)alkoxy, hydroxy, hydroxy($C_1$–$C_6$)alkyl, ($C_1$-$C_6$) alkoxy($C_1$–$C_6$)alkyl, thiol, ($C_1$–$C_6$)alkylthiol, thio($C_1$–$C_6$)alkyl or ($C_1$–$C_6$) alkyl thio($C_1$–$C_6$)alkyl.

4. A compound according to claim 2, wherein $R_5$ and $R_6$ independently represent hydrogen, halogen, hydroxy, trifluoromethyl, cyano, $C_1$–$C_3$ alkyl, or $C_1$–$C_3$ alkoxy.

5. A compound according to claim 3, wherein $R_5$ and $R_6$ independently represent hydrogen, fluoro, chloro, hydroxy, trifluoromethyl, or methyl.

6. A compound according to claim 4, wherein G is $C_1$–$C_3$ alkyl, $C_1$–$C_3$ alkoxy, or halogen.

7. A compound according to claim 4, wherein $R_5$ and $R_6$ are in the 5-and 6-position respectively and independently represent hydrogen, fluoro, chloro, methyl, ethyl, ethoxy or methoxy, and G is methyl, methoxy, or chloro.

8. A compound according to claim 5, wherein $R_7$ and $R_8$ are independently hydrogen, $C_1$–$C_6$ alkoxy, $C_1$–$C_6$ alkyl, halogen, or trifluoromethyl.

9. A compound according to claim 4 where Q is

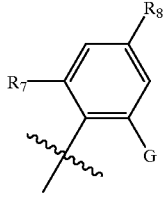

where G is $C_1$–$C_2$ alkyl and $R_7$ and $R_8$ are independently hydrogen, $C_1$–$C_2$ alkoxy, $C_1$–$C_2$ alkyl, halogen, or trifluoromethyl.

10. A compound according to claim 2, wherein Q is trimethylphenyl.

11. A compound according to claim 6, wherein Q is trimethylphenyl.

12. A compound according to claim 4, wherein $R_1$ is $C_2$–$C_4$ alkyl.

13. A compound according to claim 6, wherein $R_1$ is $C_2$–$C_3$ alkyl.

14. A compound according to claim 2, where $R_1$ is isopropyl.

15. A compound according to claim 8, wherein $R_1$ is isopropyl.

16. A compound according to claim 12, wherein $R_2$ is hydrogen.

17. A compound according to claim 13, wherein $R_2$ is hydrogen.

18. A compound according to claim 1, which is N-{[1-(4-methoxy-2-methylphenyl) benzimidazol-2-yl]methyl}-N-(methylethyl) (2,4,6-trimethylphenyl)carboxamide.

19. A compound according to claim 1, which is N-{[1-(4-methoxyphenyl) benzimidazol-2-yl]methyl}-N-(methylethyl)(2,4,6-trichlorophenyl)carboxamide.

20. A compound according to claim 1, which is N-{[1-(4-methoxyphenyl) benzimidazol-2-yl]methyl}-N-(methylethyl)(2-methylphenyl)carboxamide.

21. A compound according to claim 1, which is N-{[1-(4-methylphenyl) benzimidazol-2-yl]methyl}-N-(methylethyl)(2,4-dimethylphenyl)carboxamide.

22. A compound according to claim 1, which is N-{[1-(4-methylphenyl) benzimidazol-2-yl]methyl}-N-(methylethyl)(2-methoxyphenyl)carboxamide.

23. A compound according to claim 1, which is N-{[1-(4-methoxyphenyl) benzimidazol-2-yl]methyl}-N-(methylethyl)(3-fluoro-2-methylphenyl)carboxamide.

24. A compound according to claim 1, which is N-{[1-(4-methoxyphenyl) benzimidazol-2-yl]methyl}-N-(methylethyl)(4-chloro-2-methoxyphenyl)carboxamide.

25. A compound according to claim 1, which is N-{[1-(4-methoxyphenyl) benzimidazol-2-yl]methyl}-N-(methylethyl)(2,4-dichlorophenyl)carboxamide.

26. A compound according to claim 1, which is N-{[1-(4-methoxyphenyl) benzimidazol-2-yl]methyl}-N-(methylethyl)(2,6-dimethylphenyl)carboxamide.

27. A compound according to claim 1, which is N-{[1-(3-methoxyphenyl) benzimidazol-2-yl]methyl}-N-(methylethyl) (2,4,6-trimethylphenyl)carboxamide.

28. A compound according to claim 1, which is N-{[1-(3-methoxyphenyl) benzimidazol-2-yl]methyl}-N-(methylethyl) (2,4,6-trimethylphenyl)carboxamide.

29. A compound according to claim 1, which is N-{([1-(2-methoxyphenyl) benzimidazol-2-yl]methyl}-N-(methylethyl)(2,4,6-trimethylphenyl)carboxamide.

30. A compound according to claim 1, which is N-{[1-(2-methylphenyl) benzimidazol-2-yl]methyl}-N-(methylethyl)(2,4,6-trimethylphenyl)carboxamide.

31. A compound according to claim 1, which is N-{[1-(4-chloro-2-methylphenyl) benzimidazol-2-yl]methyl}-N-(methylethyl)(2,4,6-trimethylphenyl)carboxamide.

32. A compound according to claim 1, which is N-{[1-(4-methylphenyl) benzimidazol-2-yl]methyl}-N-(methylethyl)(2,4,6-trimethylphenyl)carboxamide.

33. A compound according to claim 1, which is N-{[1-(4-methoxyphenyl) benzimidazol-2-yl]methyl}-N-(methylethyl)(2,4,6-trimethylphenyl)carboxamide.

34. A compound according to claim 1, which is N-{[1-(2-chlorophenyl) benzimidazol-2-yl]methyl}-N-(methylethyl) (2,4,6-trimethylphenyl)carboxamide.

35. A compound according to claim 1, which is N-{[1-(4-fluorophenyl) benzimidazol-2-yl]methyl}-N-(methylethyl)(2,4,6-trimethylphenyl)carboxamide.

36. A compound according to claim 1, which is N-{[1-(4-chlorophenyl) benzimidazol-2-yl]methyl}-N-(methylethyl)(2,4,6-trimethylphenyl)carboxamide.

37. A compound according to claim 1, which is N-{[1-(4-methoxyphenyl) benzimidazol-2-yl]methyl}-N-(methylethyl)(2-fluoro-4-trifluoromethylphenyl)carboxamide.

38. A compound according to claim 1, which is N-{([1-(4-hydroxyphenyl) benzimidazol-2-yl]methyl}-N-(methylethyl)(2,4,6-trimethylphenyl)carboxamide.

39. A compound according to claim 1, which is N-{[5-fluoro-1-(4-methoxyphenyl) benzimidazol-2-yl]methyl}-N-(methylethyl)(2,4,6-trimethylphenyl)carboxamide.

40. A compound according to claim 1, which is N-{[6-methoxy-1-(4-methoxyphenyl)benzimidazol-2-yl]methyl}-N-(methylethyl) (2,4,6-trimethylphenyl)carboxamide.

41. A compound according to claim 1, which is N-{[6-ethoxy-1-(4-methoxyphenyl) benzimidazol-2-yl]methyl}-N-(methylethyl)(2,4,6-trimethylphenyl)carboxamide.

42. A compound according to claim 1, which is N-{[6-chloro-1-(4-methoxyphenyl) benzimidazol-2-yl]methyl}-N-(methylethyl)(2,4,6-trimethylphenyl)carboxamide.

43. A compound according to claim 1, which is N-{[1-(4-methoxyphenyl)-5-methylbenzimidazol-2-yl]methyl}-N-(methylethyl) (2,4,6-trimethylphenyl)carboxamide.

44. A compound according to claim 1, which is N-{[1-(2,4-dimethylphenyl) benzimidazol-2-yl]methyl)}-N-(methylethyl)(2,4,6-trimethylphenyl)carboxamide.

45. A compound according to claim 1, which is N-{[1-(4-ethoxyphenyl) benzimidazol-2-yl]methyl}-N-(methylethyl)(2,4,6-trimethylphenyl)carboxamide.

46. A compound according to claim 1, which is N-{[1-(4-hydroxy-2-methylphenyl) benzimidazol-2-yl]methyl}-N-(methylethyl)(2,4,6-trimethylphenyl)carboxamide.

47. A compound according to claim 1, which is N-{[1-(3-hydroxy-4-methoxyphenyl) benzimidazol-2-yl]methyl}-N-(methylethyl)(2,4,6-trimethylphenyl)carboxamide.

48. A compound according to claim 1, which is N-{[1-(4-methoxyphenyl) benzimidazol-2-yl]methyl}-N-(methylethyl)(2,6-dimethyl-4-methoxyphenyl) carboxamide.

49. A compound according to claim 1, which is N-{[5-fluoro-1-(4-methoxyphenyl) benzimidazol-2-yl]methyl}-N-(methylethyl)(2,6-dimethyl-4-methoxyphenyl) carboxamide.

50. A compound according to claim 1, which is N-{[1-(4-methoxyphenyl)-5 -methylbenzimidazol-2-yl]methyl)-N-(methylethyl)(2,6-dimethyl-4-methoxyphenyl) carboxamide.

51. A compound according to claim 1, which is selected from:

N-[(1-phenylbenzimidazol-2-yl)methyl]-N-(methylethyl) (2,4,6-trimethylphenyl) carboxamide;

N-[(1-phenylbenzimidazol-2-yl)methyl]-N-(methylethyl) (2,4,6-trimethylphenyl) carboxamide;

N-[(1-phenylbenzimidazol-2-yl)methyl]-N-(methylethyl) (2,4,6-trimethylphenyl) carboxamide;

N-{[1-(2,4,6-trimethylphenyl)benzimidazol-2-yl] methyl}-N-(methylethyl) (2,4,6-trimethylphenyl) carboxamide;

N-{[1-(2,4,6-trimethylphenyl)benzimidazol-2-yl] methyl}-N-(cyclopropyl) (2,4,6-trimethylphenyl) carboxamide;

N-[(i-phenylbenzimidazol-2-yl)methyl]-N-(cyclopropyl) (2,4-dimethylphenyl)carboxamide;

N-{[1-(4-methoxyphenyl)benzimidazol-2-yl]methyl}-N-(methylethyl) (4-trifluoromethylphenyl)carboxamide;

N-{[1-(4-methoxyphenyl)benzimidazol-2-yl]methyl}-N-(dimethylethyl) (2,4,6-trimethylphenyl)carboxamide;

N-{[1-(4-methoxyphenyl)benzimidazol-2-yl]methyl}(2,4,6-trimethylphenyl)carboxamide;

N-{[1-(4-(2-hydroxyethoxy)phenyl)benzimidazol-2-yl] methyl}-N-(methylethyl) (2,4,6-trimethylphenyl) carboxamide;

N-{[6-hydroxy-1-(4-methoxyphenyl)benzimidazol-2-yl] methyl}-N-(methylethyl) (2,4,6-trimethylphenyl) carboxamide;

N-{[6-chloro-1-(4-methoxyphenyl)benzimidazol-2-yl] methyl}-N-(methylethyl) (2,6-dimethyl-4-methoxyphenyl)carboxamide;

N-{[5-methyl-1-(4-methoxyphenyl)benzimidazol-2-yl] methyl}-N-(methylethyl) (4-methoxy-2-methylphenyl) carboxamide;

N-([5-amino-1-(4-methoxyphenyl)benzimidazol-2-yl] methyl}-N-(methylethyl) (2,4,6-trimethylphenyl) carboxamide;

N-{[5-methyl-1-(4-trifluoromethylphenyl)benzimidazol-2-yl]methyl}-N-(methylethyl) (2,4,6-trimethylphenyl) carboxamide;

N-{[5-methyl-1-(4-trifluoromethylphenyl)benzimidazol-2-yl]methyl}-N-(methylethyl) (4-chloro-2,6-dimethylphenyl)carboxamide;

N-{[1-(4-moxyphenyl)-5-trifluoromethylbenzimidazol-2-yl]methyl}-N-(methylethyl) (4-hydroxy-2,6-dimethylphenyl)carboxamide;

N-{[1-(4-(2-hydroxyethoxy)-2-methylphenyl) benzimidazol-2-yl]methyl}-N-(methylethyl) (2,4,6-trimethylphenyl)carboxamide; and N-{[1-(4-methoxyphenyl)-5-trifluoromethyl benzimidazol-2-yl]methyl}-N-(3-hydroxypropyl) (2,4,6-trimethylphenyl)carboxamide.

52. A compound according to claim 1, which is:

N-{[1-(4-methoxyphenyl)benzimidazol-2-yl]methyl}-N-(methylethyl) (4-chloro-2,6-dimethylphenyl)carboxamide.

53. A compound according to claim 1, which is:

N-{[5-methyl-1-(4-methoxyphenyl)benzimidazol-2-yl]methyl}-N-(methylethyl) (4-chloro-2,6-dimethylphenyl)carboxamide.

54. A compound according to claim 1, which is:

N-{[5-bromo-1-(4-methoxyphenyl)benzimidazol-2-yl]methyl}-N-(methylethyl) (2,4,6-trimethylphenyl)carboxamide.

55. A compound according to claim 1, which is:

N-{[1-(4-fluoro-2-methylphenyl)benzimidazol-2-yl]methyl}-N-(methylethyl) (2,4,6-trimethylphenyl)carboxamide.

56. A compound according to claim 1, which is:

N-{[1-(4-methoxy-2-methylphenyl)-5-trifluoromethylbenzimidazol-2-yl]methyl}-N-(methylethyl)(2,4,6-trimethylphenyl)carboxamide.

57. A compound according to claim 1, which is:

N-{[5-tert-butoxycarbamyl-1-(4-methoxyphenyl)benzimidazol-2-yl]methyl}-N-(methylethyl)(2,4,6-trimethylphenyl)carboxamide.

58. A compound according to claim 1, which is:

N-{[5-dimethylamino-1-(4-methoxyphenyl)benzimidazol-2-yl]methyl}-N-(methylethyl)(2,4,6-trimethylphenyl)carboxamide.

59. A compound according to claim 1, which is:

N-{[1-(4-hydroxy-2-methylphenyl)-5-trifluoromethyl benzimidazol-2-yl]methyl}-N-(methylethyl)(2,4,6-trimethylphenyl)carboxamide.

60. A compound according to claim 1, which is:

N-{[1-(4-(2-hydroxyethoxy)-2-methylphenyl)-5-trifluoromethylbenzimidazol-2-yl]methyl}-N-(methylethyl)(2,4,6-trimethylphenyl)carboxamide.

61. A compound according to claim 1, which is:

N-{[1-(4-methoxyphenyl)-5-trifluoromethylbenzimidazol-2-yl]methyl}-N-(methylethyl) (4-dimethylamino-2,6-dimethylphenyl)carboxamide.

62. A compound according to claim 1, which is:

N-{[5-diethylamino-1-(4-methoxyphenyl)benzimidazol-2-yl]methyl}-N-(methylethyl)(2,4,6-trimethylphenyl)carboxamide.

63. A compound according to claim 1, which is:

N-{[1-(4-methoxyphenyl)-5-trifluoromethylbenzimidazol-2-yl]methyl}-N-[1-(hydroxymethyl)ethyl](2,4,6-trimethylphenyl)carboxamide.

64. A compound according to claim 1, which is:

N-{[1-(4-methoxyphenyl)-5-trifluoromethyl benzimidazol-2-yl]methyl}-N-[2-hydroxy-1-(hydroxymethyl)ethyl](2,4,6-trimethylphenyl)carboxamide.

65. A compound according to claim 1, which is:

N-{[5-iodo-1-(4-methoxyphenyl)benzimidazol-2-yl]methyl}-N-(methylethyl) (2,4,6-trimethylphenyl)carboxamide.

66. A compound according to claim 1, which is:

N-{[1-(4-hydroxyphenyl)-5-trifluoromethyl benzimidazol-2-yl]methyl}-N-(methylethyl)(2,4,6-trimethylphenyl)carboxamide.

67. A pharmaceutical composition comprising a compound according to claim 1 and at least one pharmaceutically acceptable carrier or excipient.

* * * * *